(12) United States Patent
Wijay et al.

(10) Patent No.: US 12,290,284 B2
(45) Date of Patent: May 6, 2025

(54) UMBILICAL FORMING DEVICE TO AID IN POST-SURGICAL UMBILICAL FORMATION AND HEALING

(71) Applicants: Nandhika Wijay, Houston, TX (US); Danielle Andry Wijay, Houston, TX (US); Bandula Wijay, Friendswood, TX (US)

(72) Inventors: Nandhika Wijay, Houston, TX (US); Danielle Andry Wijay, Houston, TX (US); Bandula Wijay, Friendswood, TX (US)

( * ) Notice: Subject to any disclaimer, the term of this patent is extended or adjusted under 35 U.S.C. 154(b) by 530 days.

(21) Appl. No.: 17/854,345

(22) Filed: Jun. 30, 2022

(65) Prior Publication Data
US 2023/0285202 A1 Sep. 14, 2023

Related U.S. Application Data

(63) Continuation-in-part of application No. 17/689,210, filed on Mar. 8, 2022.

(51) Int. Cl.
| | | |
|---|---|---|
| *A61B 17/42* | (2006.01) | |
| *A61B 17/00* | (2006.01) | |
| *A61B 17/32* | (2006.01) | |
| *A61B 18/00* | (2006.01) | |
| *A61F 13/00* | (2024.01) | |
| *A61F 13/14* | (2006.01) | |

(52) U.S. Cl.
CPC .............. *A61B 17/42* (2013.01); *A61B 17/32* (2013.01); *A61F 13/148* (2013.01);
(Continued)

(58) Field of Classification Search
CPC ......... A61B 17/42; A61B 17/32; A61B 17/00; A61B 17/0057; A61B 17/02;
(Continued)

(56) References Cited

U.S. PATENT DOCUMENTS

2011/0098681 A1* 4/2011 Djurivic ............ A61B 17/0057
606/195
2013/0245527 A1* 9/2013 Croizat ................ A61F 13/148
604/319

(Continued)

*Primary Examiner* — Alireza Nia
*Assistant Examiner* — Daniel A Miller
(74) *Attorney, Agent, or Firm* — Ergenzinger IP Law; Ed Ergenzinger

(57) ABSTRACT

An Umbilical Forming Device is provided for enhancing healing of an umbilical wound, scar, or contour in a subject following a surgery involving the umbilicus, including but not limited to an abdominoplasty. The Umbilical Forming Device comprises a flexible body configured for use during healing of the umbilical wound. In some aspects, the flexible body is free of any holes. In other aspects, the flexible body comprises a wall, wherein the wall defines a hollow cavity and comprises one or more holes configured to facilitate drainage of secretions and/or ventilation of the umbilical wound, including wherein the flexible body further comprises proximal and/or distal openings configured to facilitate observation of the healing of the umbilical wound, removal of any secretions from the umbilical wound, and/or administration of one or more therapeutic agents to the umbilical wound. Methods of use and kits comprising the devices disclosed herein are also provided.

2 Claims, 8 Drawing Sheets

(52) U.S. Cl.
CPC ............... *A61B 2017/00761* (2013.01); *A61B 2018/00601* (2013.01); *A61F 2013/00382* (2013.01); *A61F 2013/00578* (2013.01)

(58) Field of Classification Search
CPC ........... A61B 2017/00761; A61B 2017/00637; A61B 2017/00641; A61B 2018/00601; A61B 90/02; A61F 5/30; A61F 13/148; A61F 2/0063; A61F 2/02; A61F 2/0068; A61F 2/0009; A61F 2013/00382; A61F 2013/00578; A61F 2013/15032; A61F 2013/1504

USPC ............................................ 602/61; 128/887
See application file for complete search history.

(56) References Cited

U.S. PATENT DOCUMENTS

| | | | |
|---|---|---|---|
| 2014/0148827 A1* | 5/2014 | Odermatt | A61B 17/0057 606/151 |
| 2016/0045220 A1* | 2/2016 | Wachli | A61B 17/34 600/204 |
| 2016/0151195 A1* | 6/2016 | Vekios | A61B 17/0057 602/61 |

* cited by examiner

UMBILICAL FORMING DEVICE TO AID IN POST-SURGICAL UMBILICAL FORMATION AND HEALING

FIELD OF INVENTION

The field of invention is the use of an umbilical forming device to aid in the healing of a post-surgical umbilical wound, scar, or contour following a surgery involving the umbilicus, including but not limited to an abdominoplasty. The device also aids in the detection of healing status and is also useful for applying dynamic pressure on the umbilical wound via a series of devices of increasing shore strengths. The device is uniquely designed to detect the healing process of the wound, introduce therapeutic substances as needed into the wound, and contouring of the scar to the desired shape.

BACKGROUND

The umbilicus, also known as the navel or belly button, is a concave area on the human body that marks the previous connection to that individual's mother during fetal life. The umbilical cord is fully formed by week 7, and is composed of a connecting stalk, vitelline duct, and umbilical vessels surrounding an amniotic membrane. The umbilical vessels carry fetal blood back and forth to the placenta, and thereby transport oxygenated blood and nutrients to the fetus and deoxygenated blood and waste products to the placenta. After birth, the umbilical stump falls off leaving a scarred tissue remnant known as the navel or belly button.

An abdominoplasty is a reconstructive procedure that removes excessive skin in individuals who have lost weight or completed childbirth. Initially, during an abdominoplasty, the original umbilicus is excised externally with a scalpel to separate the umbilicus from the abdominal skin. Next the abdominal skin and fat is elevated above the superficial rectus fascia. Once the umbilicus is surgically identified, the umbilical stalk is isolated from the surrounding tissue. Soon after, the excess skin is pulled down and a new incision is made to pull out the original umbilicus. Once the umbilicus is pulled through, the umbilicus is sutured in place with either absorbable or permanent sutures. The umbilicus will now begin its four stages of wound healing: Hemostasis Phase, Inflammatory Phase, Proliferative Phase, and Maturation Phase. In the Hemostasis Phase, the umbilicus wound is forming its clot. In the Inflammatory Phase, white blood cells come to remove any infection. In the Proliferative Phase, the wound starts laying down a collagen and extracellular matrix. In this phase the wound starts to contract. In the Maturation Phase, the collagen remodels to form type III collagen to type I collagen. This phase begins around the three-week mark.

In an abdominoplasty, the umbilicus wound can take a minimum of six weeks to heal. At six weeks, the scar has the most of its strength. Over the next three months the umbilicus will continue to tighten and contract. However, umbilical healing can have complications, the most common of which is delayed wound healing. Delayed wound healing can be due to pressure on the wound, poor nutrition, or poor vascularity. Another possible complication is an infection of the umbilicus. Infection can be caused by bacterial exposure or poor wound care. A third common complication is that the scar contracts too much, closing the umbilicus wound leaving no navel or belly button after surgery.

The current treatment after surgery for umbilical wound care is the use of lubricated medical gauze. Lubricated medical gauze is the treatment used in a multitude of wounds throughout the body. Another treatment option is the use of antimicrobial ointment placed manually into the wound.

What is needed and addressed by the present invention is a device that is shaped like an umbilicus, and in doing so, the scar wound will heal in the contour of the normal shape of a navel. In addition, the current invention has uniquely designed holes around the device to detect abnormal drainage from the wound. These holes, including the opening at its proximal end, can aid in the early detection of an infection. Similarly, these holes allow the individual to introduce any desired therapeutic substances to the healing wound.

SUMMARY OF INVENTION

To address the foregoing problems, in whole or in part, and/or other problems that may have been observed by persons skilled in the art, the present disclosure provides compositions and methods as described by way of example as set forth below.

In one embodiment, an Umbilical Forming Device is provided for enhancing healing of an umbilical wound, scar, or contour in a subject following a surgery involving the umbilicus, wherein the Umbilical Forming Device comprises a flexible body configured for use during healing of the umbilical wound. In some aspects, the flexible body is free of any holes.

In another embodiment, an Umbilical Forming Device is provided for enhancing healing of an umbilical wound, scar, or contour in a subject following a surgery involving the umbilicus, wherein the Umbilical Forming Device comprises a flexible body configured for use during healing of the umbilical wound, wherein the flexible body comprises a wall, and wherein the wall defines a hollow cavity and comprises one or more holes configured to facilitate drainage of secretions and/or ventilation of the umbilical wound. In some aspects, the flexible body comprises a proximal and/or a distal opening configured to facilitate observation of the healing of the umbilical wound, removal of any secretions from the umbilical wound, and/or administration of one or more therapeutic agents to the umbilical wound.

In some aspects, any of the Umbilical Forming Devices described herein are configured for use during healing of the umbilical wound wherein:
a) healing of the umbilical wound lasts up to 8 weeks after the surgery involving the umbilicus;
b) healing of the umbilical wound lasts from 4 to 8 weeks after the surgery involving the umbilicus;
c) healing of the umbilical wound lasts approximately 6 weeks following the surgery involving the umbilicus; or
d) healing of the umbilical wound lasts until the umbilical wound has scarred over and/or a medical professional determines that the umbilical wound has healed.

In other aspects, for any of the Umbilical Forming Devices described herein, the surgery involving the umbilicus comprises an abdominoplasty.

In other aspects, for any of the Umbilical Forming Devices described herein, the flexible body has a substantially rectangular shape having a curved profile superiorly and a generally a flat shape inferiorly. In other aspects, the flexible body has a symmetrical profile. In other aspects, the flexible body has a shape configured to facilitate contouring a scar from the umbilical wound to facilitate healing into an aesthetically pleasing umbilical structure. In other aspects, the flexible body is configured to allow dynamic movement synchronous with motion of the umbilical wound, thereby minimizing pressure points within the umbilical wound.

In other aspects, for any of the Umbilical Forming Devices described herein, the flexible body further comprises protrusions positioned proximal to the distal opening and configured to facilitate anchoring the Umbilical Forming Device within the umbilical wound, and wherein the flexible body comprises at least one groove or a portion thereof configured to contain at least one therapeutic agent.

In other aspects, for any of the Umbilical Forming Devices described herein, the flexible body comprises a soft rubber-like bio-compatible material. In some aspects, the soft rubber-like material is silicone, ethylene propylene diene monomer (EPDM), or Polyurethane.

In other aspects, for any of the Umbilical Forming Devices described herein, a method of enhancing healing of an umbilical wound, scar, or contour in a subject following a surgery involving the umbilicus is provided, comprising the steps of:
 a) anchoring any of the Umbilical Forming Devices described herein within the umbilical wound of the subject; and
 b) observing the healing of the umbilical wound, removing any secretions from the umbilical wound, administering one or more therapeutic agents to the umbilical wound, and/or replacing the Umbilical Forming Device with a series of Umbilical Forming Devices of increasing shore strengths to apply dynamic pressure on the umbilical wound.

In other aspects, step (b) of the method of enhancing healing of an umbilical wound, scar, or contour comprises replacing the Umbilical Forming Device with a series of Umbilical Forming Devices of increasing shore strengths over a period of:
 i) up to 8 weeks after the surgery involving the umbilicus;
 ii) from 4 to 8 weeks after the surgery involving the umbilicus;
 iii) approximately 6 weeks following the surgery involving the umbilicus; or
 iv) until the umbilical wound has scarred over and/or a medical professional determines that the umbilical wound has healed.

In other aspects, for any of the Umbilical Forming Devices described herein, a packaged kit is provided, comprising any of the Umbilical Forming Devices described herein, wherein the packaged kit is configured to provide the Umbilical Forming Device in a sterile condition to a user.

Additional features of the invention will be or will become apparent to one with skill in the art upon examination of the following figures and detailed description. It is intended that all such additional features and advantages be included within this description, be within the scope of the invention, and be protected by the accompanying claims.

BRIEF DESCRIPTION OF DRAWINGS

Figure 1:
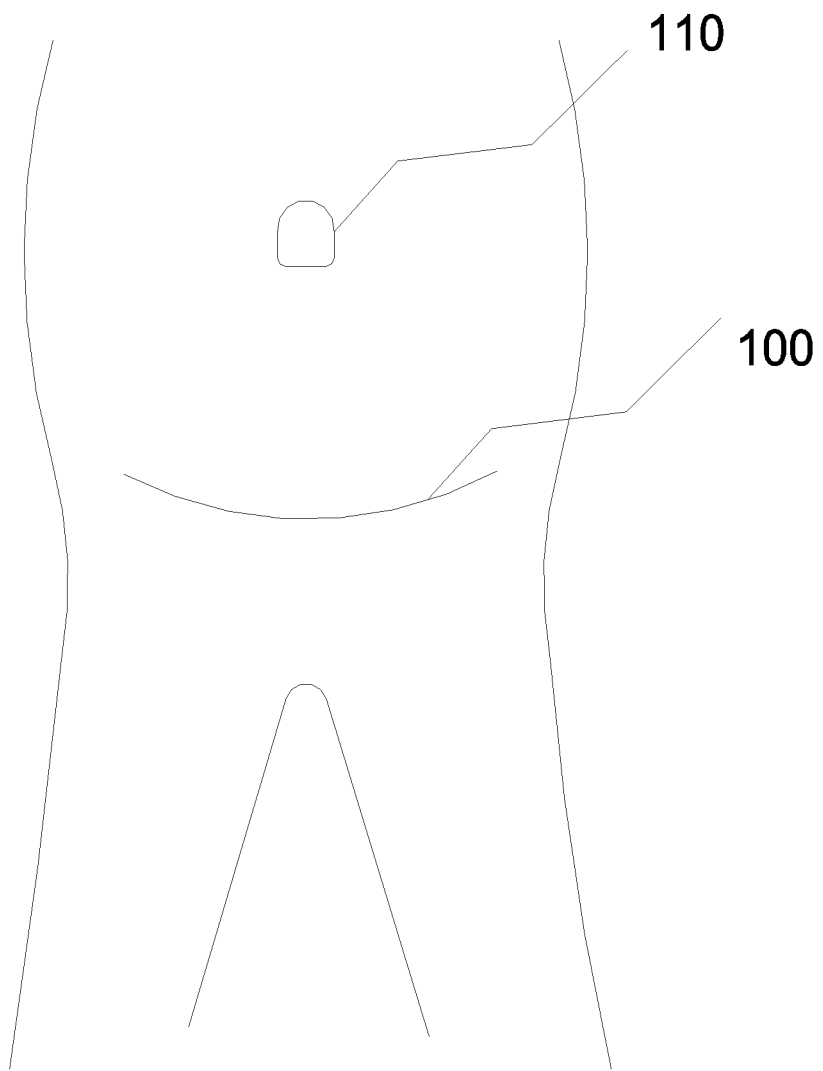

Having thus described the subject matter of the present invention in general terms, reference will now be made to the accompanying drawings, which are not necessarily drawn to scale, and wherein:

FIG. 1 shows a typical incision for an abdominoplasty made near the bikini line.

Figure 2:
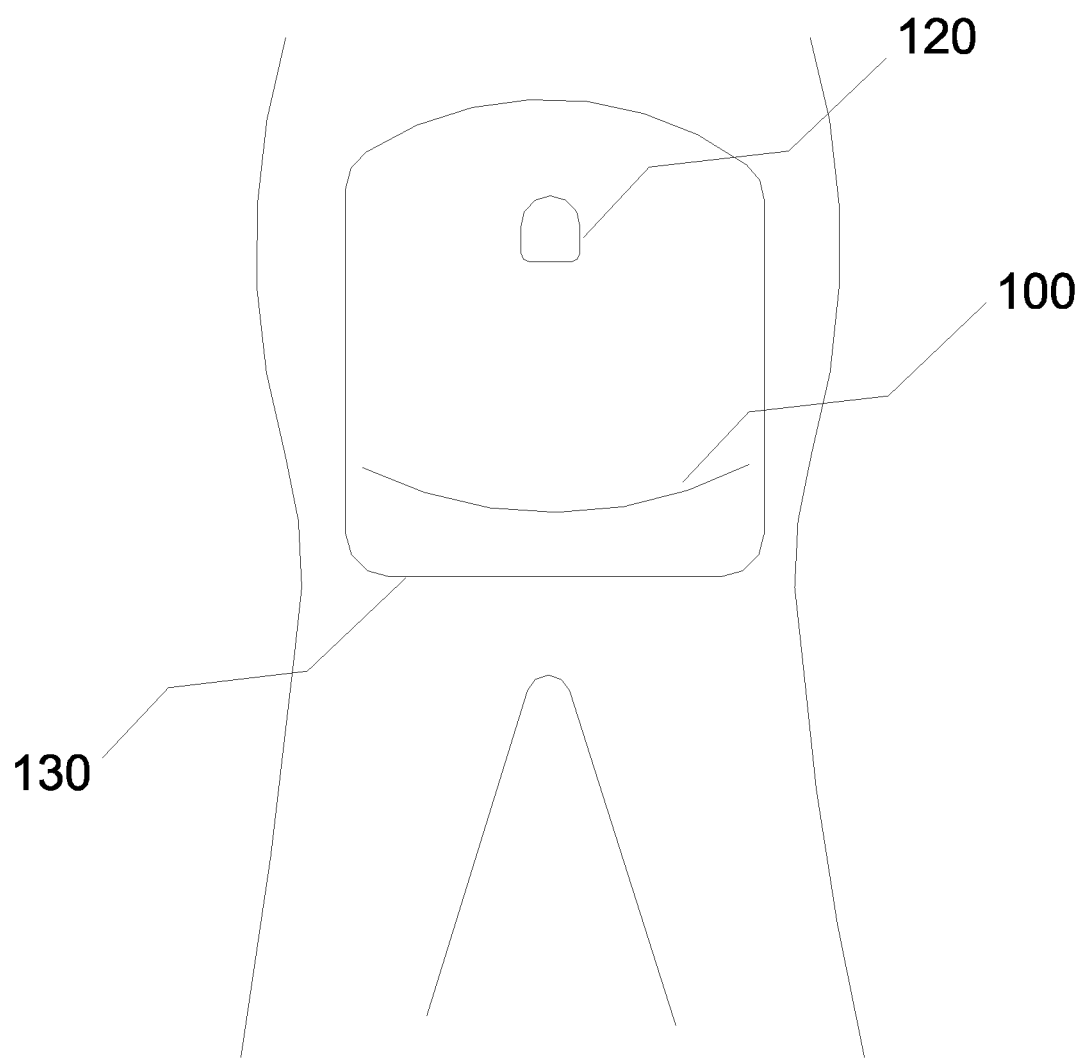

FIG. 2 shows a skin flap that is drawn down over the previous incision shown in FIG. 1.

Figure 3:
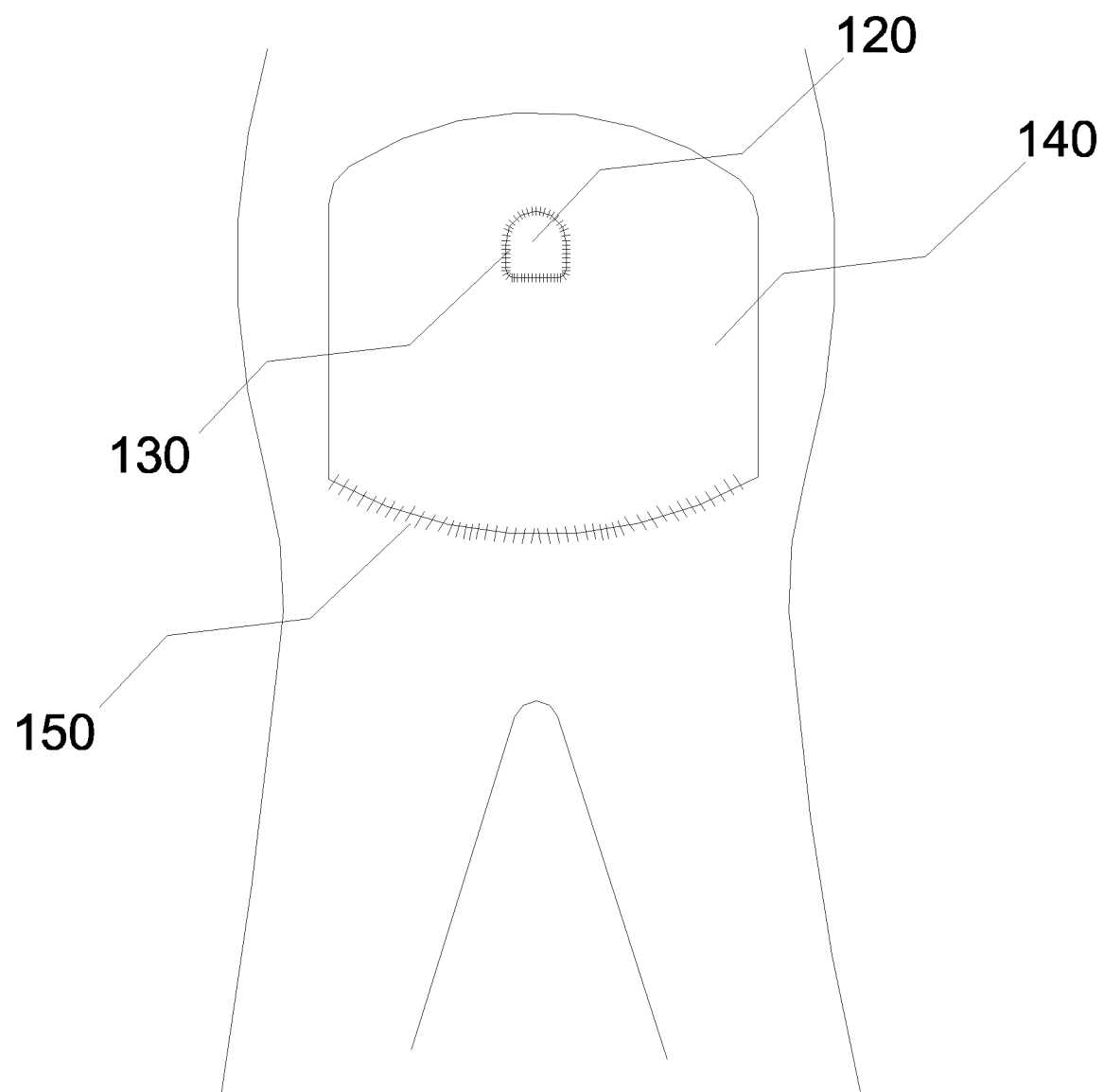

FIG. 3 shows a newly formed belly button at the appropriate location.

Figure 4:
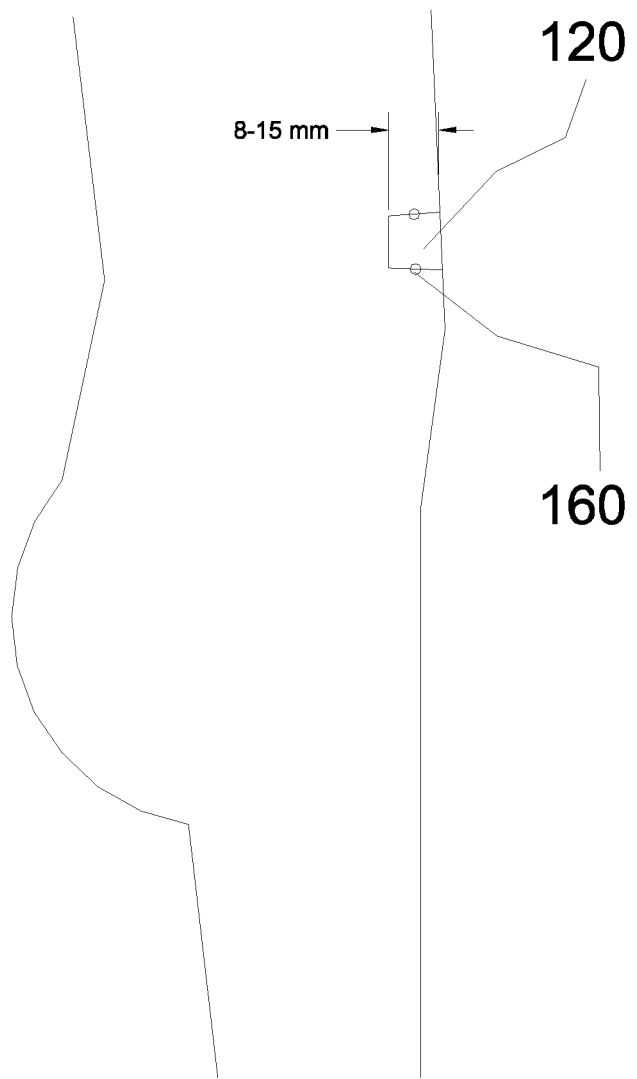

FIG. 4 shows a side view of the newly formed belly button shown in FIG. 3.

Figure 5:
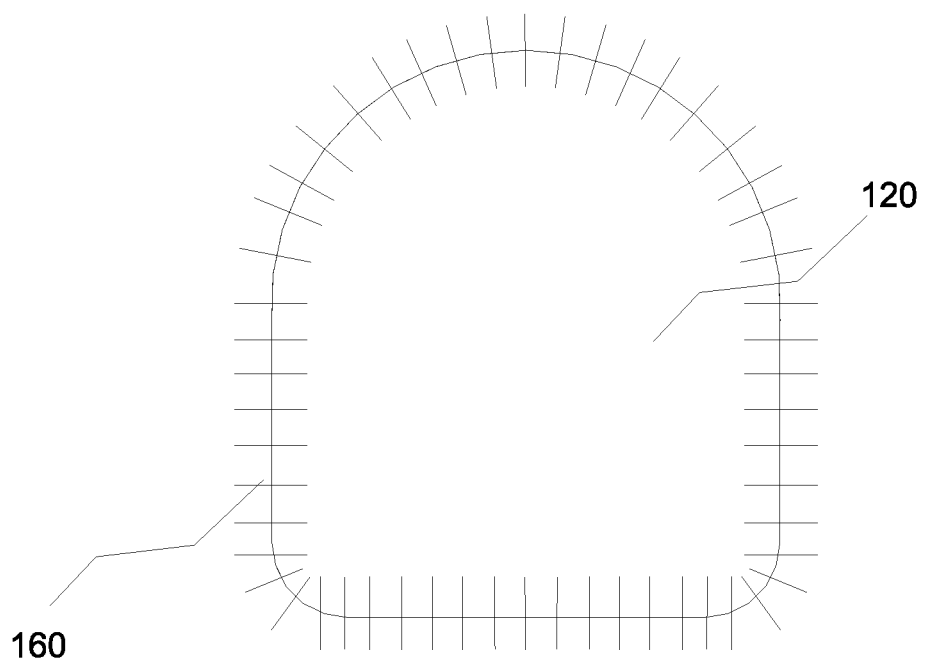

FIG. 5 shows the anatomical front view of the newly formed belly button.

Figure 6:
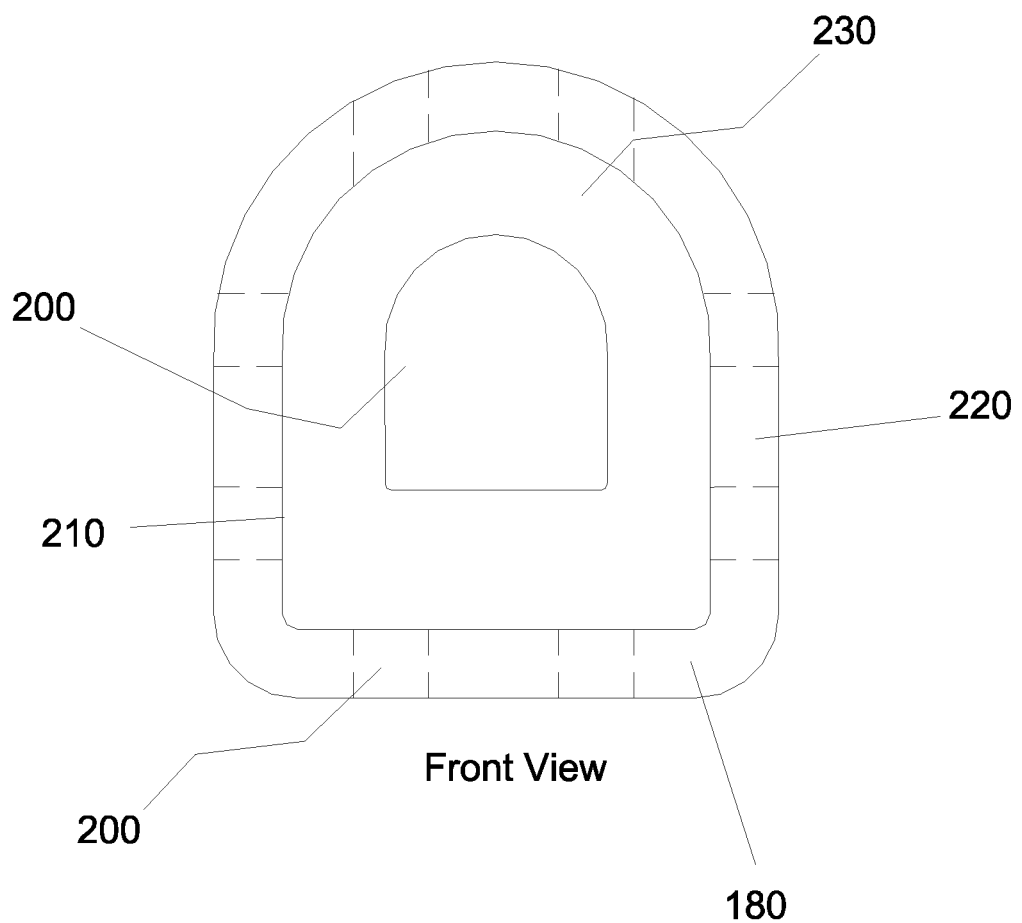
Figure 6:
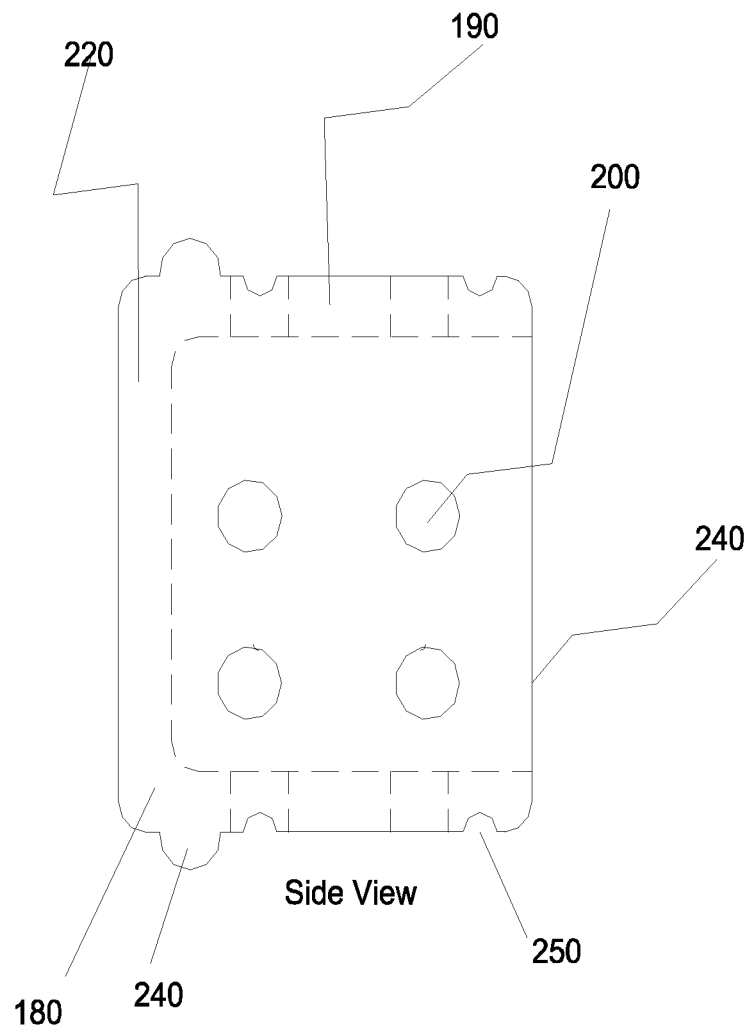
Figure 6:
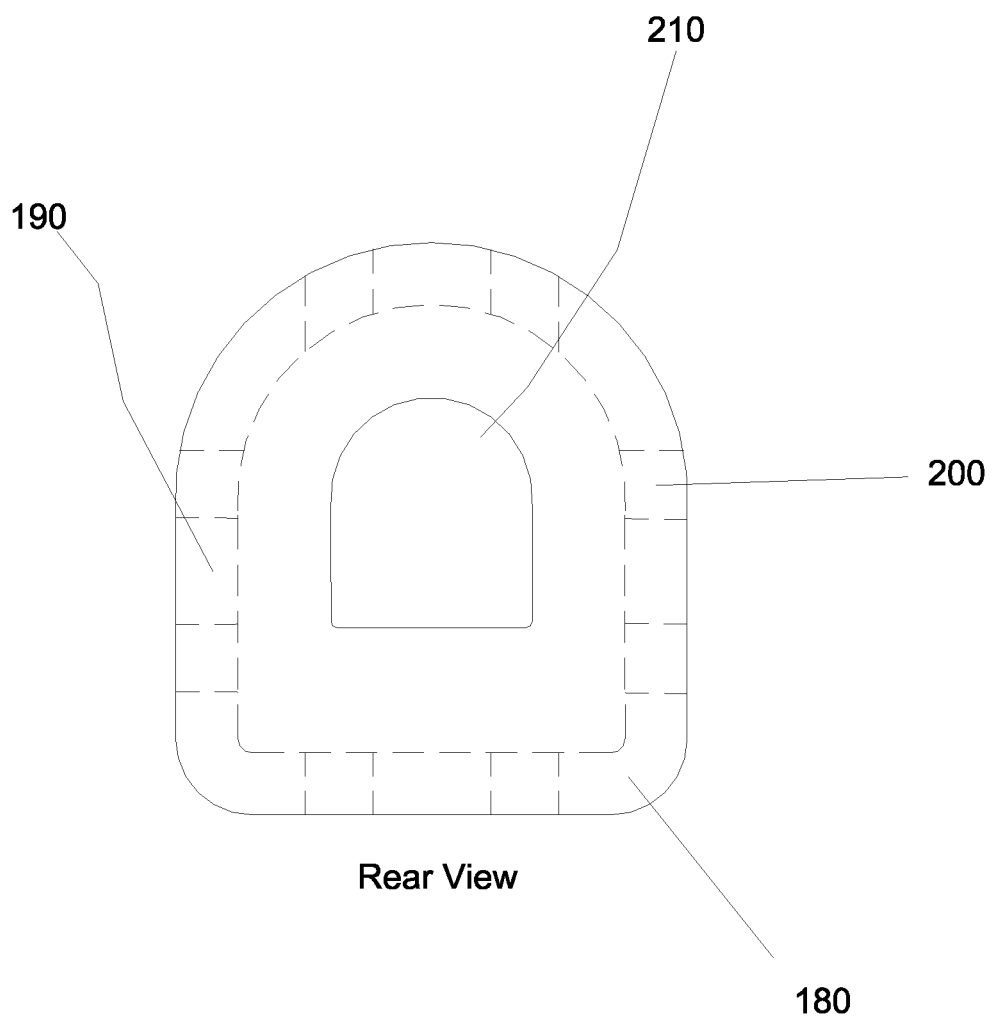

FIG. 6a shows a front view of the Umbilical Forming Device of the present invention.

FIG. 6b shows a rear view of the Umbilical Forming Device of the present invention.

FIG. 6c shows a side view of the Umbilical Forming Device of the present invention.

DETAILED DESCRIPTION

The subject matter of the present invention now will be described more fully hereinafter with reference to the accompanying drawings, in which some, but not all embodiments of the subject matter of the present invention are shown. Like numbers refer to like elements throughout. The subject matter of the present invention may be embodied in many different forms and should not be construed as limited to the embodiments set forth herein; rather, these embodiments are provided so that this disclosure will satisfy applicable legal requirements. Indeed, many modifications and other embodiments of the subject matter of the present invention set forth herein will come to mind to one skilled in the art to which the subject matter of the present invention pertains having the benefit of the teachings presented in the foregoing descriptions and the associated drawings. All illustrations of the drawings are for the purpose of describing selected versions of the present invention and are not intended to limit the scope of the present invention. Therefore, it is to be understood that the subject matter of the present invention is not to be limited to the specific embodiments disclosed and that modifications and other embodiments are intended to be included within the scope of the appended claims.

Umbilical Forming Device to Aid in Post-Surgical Umbilical Formation and Healing Abdominoplasty surgery is where the excess skin is removed from the persons trunk anatomy to reduce the bulge in the abdomen, and the original belly button is excised, and a new bell button is artificially created by the surgeon. In doing so, the new structure must be anatomically similar to the de novo structure. This process is quite complicated, and the end result depends on how the wound has healed during the post-surgical recovery period. The appearance of the belly button should be similar to the pre-surgical anatomy and need to be aesthetically acceptable to the patient and should be similar to the normal anatomy of a belly button.

The wound healing process can greatly affect the final anatomy of the shape of the post-surgical belly button. The present invention describes a procedure and a device that will help the wound healing process while maintaining the desired shape and also be able to detect the healing process of the wound, introduce therapeutic substances into the wound, and contouring of the scar.

Typical cross section of the belly button is somewhat rectangular with rounded edges at the superior wall of the belly button and is with smooth corners. Typically, the belly button has a width of 8-12 mm and a height of 10-15 mm. The depth can vary between 8 to 15 mm depending on the person and how the original wound has healed after the childbirth. One of the main challenges to proper healing of the wound is to provide the necessary treatments to the wound during the wound healing process. Thus, proper blood circulation and keeping the wound free of any pathogens that can infect the wound are of paramount importance.

Any secretions oozing out should also be properly removed. And for aesthetic reasons the anatomy after the wound is healed must have the desired shape. Above all the surgeon should be able to observe the wound healing process without having to totally remove the umbilical healing device from the navel.

In the current state of the art, a gauze plug impregnated with therapeutic agent is pushed in the newly constructed belly button cavity. There are several drawbacks in this method as it does not provide means to observe the process of healing in the post-surgical period while the gauze is in place. In addition, as the gauze plug becomes quite rigid once it is soaked with body secretions and therefore it can also cause pressure necrosis. In addition, if the wound has a current infection and is draining purulence, the gauze plug traps the purulence, potentially worsening the wound and infection. As the plug is almost a solid structure it is quite difficult, or almost impossible, to observe the state of the wound during the wound healing process while the gauze plug is in place.

Thus, there is no method facilitating the drainage of any secretions arising from the wound, nor have physicians or other healthcare providers been able to refresh the therapeutic treatment that is often required. There is also no attempt to fix the desired anatomy of the belly button in order to make the final healed anatomy similar to the natural belly button anatomy.

The proposed solution is a device having a flexible body, the umbilical forming device, having an inner open space, contoured to mimic the natural—de novo shape of the belly button, provided with openings in the said flexible body to facilitate the drainage of any secretions from the wound as well as provide a path to provide therapeutic agents to the wound at the same time. The open inner chamber provides the opportunity for the surgeon to observe the wound healing process, observe any infection thereof, and as well as provide means to remove any secretions. Also, these openings allow for wound to have airflow, ventilation, to the wound. Airflow can help with temperature control of the wound and oxygenation. The flexible nature of the body allows of the constant dynamic motion of the wound and will not cause pressure points in the wound, that otherwise can cause pressure necrosis. Flexible body allows appropriate contact to the wound to allow for improved contour without causing undue pressure necrosis.

In the proposed embodiment, it is also possible to provide such structures as a "collar" or "fin", at its distal end to help anchor the embodiment properly and securely within the newly structured belly button cavity.

In summary, the present invention proposes an umbilical forming device to be used during a surgery involving the umbilicus, including but not limited to an abdominoplasty, where the surgeon creates a new belly button. And in the present invention, the device facilitates the creation of a more attractive belly button that is similar to the native de novo belly button, while providing all the essential requirements for proper healing, such as drainage of secretions and therapeutic treatment with improved formation of scar contour while being able to observe the wound healing process.

Turning now to FIG. 1, a typical surgical procedure is shown where a skin incision (100) similar to the one shown in the diagram is made by the surgeon. The native belly button is marked as (110). The skin is separated from the muscle layer until the desired length is achieved and the native belly button (110) is exercised leaving the umbilical in place. The loose skin is then drawn down inferiorly to the desired extent and the extra portion of the skin and fat is removed and the remaining skin is sutured back at the first incision (100).

FIG. 2 shows that a new hole is cut in the skin after the procedure as in FIG. 1. And the previously excised umbilical is sutured at the newly formed belly button (120) in the skin.

FIG. 3. Shows the newly created belly button (120) been sutured to the original belly button (110) using sutures (130). The skin after removing the excess, is sutured to the first incision (100) using sutures (150).

FIG. 4 shows a side view of the newly formed belly button (120) having a depth of about 8-15 mm or as determined by the surgeon and sutured at about halfway at a location (160) in the belly button structure. The healing wound of the belly button can be of different depths from the surface depending on the original stalk of the native belly button.

FIG. 5 shows the frontal view of the newly formed belly button (120) having a generally a rectangular shape having rounded large radius edges in the interior wall at the superior edge and generally square edge in the interior wall at the inferior edge. The Sutures (160) are normally placed around the middle of the wound between the native umbilicus and the abdominal skin. However, there are no sharp edges at the inferior wall. Also, the shape of the belly button can be circular, oval, rectangular or any desired shape.

The Umbilical Forming Device (180) is a temporary implant device as in FIG. 6a—(Front View) and is made from a soft material such as silicone rubber, EPDM rubber, Polyethylene or any other flexible bio-compatible material suitable for implant into a wound. The general shape of the implant is made to match the desired outcome of the healed belly button. The device is made from flexible rubbery material allowing the device to deform and adjust to different movements of the trunk and thereby preventing the formation of pressure necrosis.

The shape of the Umbilical Forming Device (180) defines a hollow cavity (230) with an opening in the proximal end generally rectangular in nature, as shown in FIG. 6b, with a width ranging from 8-12 mm and height ranging from 10-15 mm. The top edges are circular in nature and the bottom edges are generally square with chamfered edges. The depth of the Umbilical Forming Device (180) is between 8 and 15 mm and however the shape of the belly button can be any shape desired by the surgeon.

The Umbilical Forming Device (180) has multiple bleed holes (200) on its walls as shown in FIG. 6a, 6b, 6c. These holes are provided in all walls of the Umbilical Forming Device (180). The holes typically are 3 mm in diameter, although both a multitude of smaller holes of a lesser number of larger holes may also be provided to achieve the same goal. The front opening (210), as shown in FIG. 6a, is generally of similar shape as the Umbilical Forming Device (180) having a generally uniform wall (220) of 2-3 mm thickness. The opening in the rear (210), facing the persons abdomen, as shown in FIG. 6c, is also generally similar to the shape of the umbilical forming device, but generally is smaller than the opening in the front. In addition, the rear wall or at a location close to it can be provided with a lip (240), as shown in FIG. 6b to aid as an anchor to keep the device in place within the wound cavity.

The Umbilical Forming Device (180) is provided with at least one groove or a portion thereof (250), which can be on its circumferential surface, in its outer surface that helps therapeutic agents to be placed before it is placed in the umbilical wound.

These holes provided will facilitate the flow of the therapeutic agents that are either provide when the umbilical forming device is supplied to the user or can be introduced from a syringe once the device in positioned in the umbilical wound. In addition, the holes provide means for any secretions to pass out of the wound and helps to keep the wound dry. Additionally, the surgeon can easily clean the wound area using a cotton swab or a similar method by cleaning the hollow cavity (230) as well as provide fresh batch of therapeutic agents as well.

The umbilical forming device can be provided to the user packaged with antimicrobial or other therapeutic agents or without any medicinal component depending on user preference and thereby providing the surgeon or the user the flexibility to use whichever the type of therapeutic agent that the user prefers.

In a normal procedure once, the surgeon attaches the existing umbilical to the newly created opening in the skin, it is sutured in place. Once this step is completed the umbilical forming device, having therapeutic agent is pushed into the newly created belly button and a tape is placed to hold the umbilical forming device in place, until the wound is fully healed. During the wound healing period, surgeon may remove the tape to inspect the wound healing process, clean the wound, remove any drainage or pus present and or add additional healing medicine to the wound.

In addition, during the wound healing process surgeon may also completely replace the present umbilical forming device, properly clean the wound and reuse the device or replace it with a new unit.

Accordingly, in one embodiment, an Umbilical Forming Device is provided for enhancing healing of an umbilical wound, scar, or contour in a subject following a surgery involving the umbilicus, wherein the Umbilical Forming Device comprises a flexible body configured for use during healing of the umbilical wound. In some aspects, the flexible body is free of any holes.

In another embodiment, an Umbilical Forming Device is provided for enhancing healing of an umbilical wound, scar, or contour in a subject following a surgery involving the umbilicus, wherein the Umbilical Forming Device comprises a flexible body configured for use during healing of the umbilical wound, wherein the flexible body comprises a wall, and wherein the wall defines a hollow cavity and comprises one or more holes configured to facilitate drainage of secretions and/or ventilation of the umbilical wound. In some aspects, the flexible body comprises a proximal and/or a distal opening configured to facilitate observation of the healing of the umbilical wound, removal of any secretions from the umbilical wound, and/or administration of one or more therapeutic agents to the umbilical wound.

All wounds bend and flex with body motion, however, due to the flexible nature of the Umbilical Forming Devices described herein, the devices prevent unnecessary pressure on the wound that can cause necrosis.

In some aspects, any of the Umbilical Forming Devices described herein are configured for use during healing of the umbilical wound wherein:
  a) healing of the umbilical wound lasts up to 8 weeks after the surgery involving the umbilicus;
  b) healing of the umbilical wound lasts from 4 to 8 weeks after the surgery involving the umbilicus;
  c) healing of the umbilical wound lasts approximately 6 weeks following the surgery involving the umbilicus; or
  d) healing of the umbilical wound lasts until the umbilical wound has scarred over and/or a medical professional determines that the umbilical wound has healed.

In other aspects, for any of the Umbilical Forming Devices described herein, the surgery involving the umbilicus comprises an abdominoplasty.

In other aspects, for any of the Umbilical Forming Devices described herein, the flexible body has a substantially rectangular shape having a curved profile superiorly and a generally a flat shape inferiorly. In other aspects, the flexible body has a symmetrical profile. In other aspects, the flexible body has a shape configured to facilitate contouring a scar from the umbilical wound to facilitate healing into an aesthetically pleasing umbilical structure. In other aspects, the flexible body is configured to allow dynamic movement synchronous with motion of the umbilical wound, thereby minimizing pressure points within the umbilical wound.

In other aspects, for any of the Umbilical Forming Devices described herein, the flexible body further comprises protrusions positioned proximal to the distal opening and configured to facilitate anchoring the Umbilical Forming Device within the umbilical wound, and wherein the flexible body comprises at least one groove or a portion thereof configured to contain at least one therapeutic agent.

In other aspects, for any of the Umbilical Forming Devices described herein, the flexible body comprises a soft rubber-like bio-compatible material. In some aspects, the soft rubber-like material is silicone, ethylene propylene diene monomer (EPDM), or Polyurethane.

In other aspects, for any of the Umbilical Forming Devices described herein, a method of enhancing healing of an umbilical wound, scar, or contour in a subject following a surgery involving the umbilicus is provided, comprising the steps of:
  a) anchoring any of the Umbilical Forming Devices described herein within the umbilical wound of the subject; and
  b) observing the healing of the umbilical wound, removing any secretions from the umbilical wound, administering one or more therapeutic agents to the umbilical wound, and/or replacing the Umbilical Forming Device with a series of Umbilical Forming Devices of increasing shore strengths to apply dynamic pressure on the umbilical wound.

Furthermore, by replacing the Umbilical Forming Device with a series of Umbilical Forming Devices of increasing shore strengths, the least pressure is placed on the umbilical wound early in the healing process while more pressure is placed on the umbilical wound later in the healing process when the wound can tolerate firmer hardness. Accordingly, in other aspects, step (b) of the method enhancing healing of an umbilical wound, scar, or contour comprises replacing the Umbilical Forming Device with a series of Umbilical Forming Devices of increasing shore strengths over a period of:
  i) up to 8 weeks after the surgery involving the umbilicus;
  ii) from 4 to 8 weeks after the surgery involving the umbilicus;
  iii) approximately 6 weeks following the surgery involving the umbilicus; or
  iv) until the umbilical wound has scarred over and/or a medical professional determines that the umbilical wound has healed.

In some aspects, the series of Umbilical Forming Devices of increasing shore strengths comprise shore strengths of about 25, 35, 45, and/or 60.

In other aspects, for any of the Umbilical Forming Devices described herein, a packaged kit is provided, comprising any of the Umbilical Forming Devices described herein, wherein the packaged kit is configured to provide the Umbilical Forming Device in a sterile condition to a user.

General Definitions

The terms "patient," "individual," or "subject" are used interchangeably herein, and refer to a mammal, particularly, a human, and more particularly, a human in need of a surgery involving the umbilicus, including but not limited to an abdominoplasty.

Terms and phrases used in this document, and variations thereof, unless otherwise expressly stated, should be construed as open ended as opposed to limiting. As examples of the foregoing: the term "including" should be read as mean "including, without limitation" or the like; the term "example" is used to provide exemplary instances of the item in discussion, not an exhaustive or limiting list thereof; and adjectives such as "conventional," "traditional," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although item, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount, or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the subject matter of the present invention. For example, the term "about," when referring to a value can be meant to encompass variations of, in some embodiments ±100%, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. Although the foregoing subject matter has been described in some detail by way of illustration and example for purposes of clarity of understanding, it will be understood by those skilled in the art that certain changes and modifications can be practiced within the scope of the appended claims.

We claim:

1. A method of enhancing healing of an umbilical wound, scar, or contour in a subject following a surgery involving an umbilicus, comprising the steps of:
    a) anchoring an Umbilical Forming Device within the umbilical wound of the subject, wherein the Umbilical Forming Device comprises a flexible body configured for use during healing of the umbilical wound; and
    b) observing the healing of the umbilical wound, removing any secretions from the umbilical wound, administering one or more therapeutic agents to the umbilical wound, and/or replacing the Umbilical Forming Device with a series of Umbilical Forming Devices of increasing shore strengths to apply dynamic pressure on the umbilical wound;

wherein step (b) comprises replacing the Umbilical Forming Device with a series of Umbilical Forming Devices of increasing shore strengths over a period of:
    i) up to 8 weeks after the surgery involving the umbilicus;
    ii from 4 to 8 weeks after the surgery involving the umbilicus;
    iii) approximately 6 weeks following the surgery involving the umbilicus; or
    iv) until the umbilical wound has scarred over and/or a medical professional determines that the umbilical wound has healed.

2. A method of enhancing healing of an umbilical wound, scar, or contour in a subject following a surgery involving an umbilicus, comprising the steps of:
    a) anchoring an Umbilical Forming Device within the umbilical wound of the subject, wherein the Umbilical Forming Device comprises a flexible body configured for use during healing of the umbilical wound, wherein the flexible body comprises a wall, and wherein the wall defines a hollow cavity and comprises one or more holes configured to facilitate drainage of secretions and/or ventilation of the umbilical wound; and
    b) observing the healing of the umbilical wound, removing any secretions from the umbilical wound, administering one or more therapeutic agents to the umbilical wound, and/or replacing the Umbilical Forming Device with a series of Umbilical Forming Devices of increasing shore strengths to apply dynamic pressure on the umbilical wound;

wherein step (b) comprises replacing the Umbilical Forming Device with a series of Umbilical Forming Devices of increasing shore strengths over a period of:
 i) up to 8 weeks after the surgery involving the umbilicus;
 ii) from 4 to 8 weeks after the surgery involving the umbilicus;
 iii) approximately 6 weeks following the surgery involving the umbilicus; or
 iv) until the umbilical wound has scarred over and/or a medical professional determines that the umbilical wound has healed.

\* \* \* \* \*